US011123453B2

(12) United States Patent
Yuki et al.

(10) Patent No.: US 11,123,453 B2
(45) Date of Patent: Sep. 21, 2021

(54) LIQUID EMBOLIC AGENT COMPOSITION

(71) Applicants: SHINSHU UNIVERSITY, Matsumoto (JP); Ichiro Yuki, Irvine, CA (US)

(72) Inventors: Ichiro Yuki, Irvine, CA (US); Kousaku Ohkawa, Nagano (JP); Takaomi Nomura, Nagano (JP)

(73) Assignees: SHINSHU UNIVERSITY, Matsumoto (JP); Ichiro Yuki, Irvine, CA (US)

( * ) Notice: Subject to any disclaimer, the term of this patent is extended or adjusted under 35 U.S.C. 154(b) by 0 days.

(21) Appl. No.: 16/334,894

(22) PCT Filed: Feb. 21, 2018

(86) PCT No.: PCT/JP2018/006147
§ 371 (c)(1),
(2) Date: Mar. 20, 2019

(87) PCT Pub. No.: WO2019/163012
PCT Pub. Date: Aug. 29, 2019

(65) Prior Publication Data
US 2020/0009290 A1   Jan. 9, 2020

(51) Int. Cl.
*A61L 24/10* (2006.01)
*A61K 49/04* (2006.01)
*A61P 7/04* (2006.01)
*A61L 24/00* (2006.01)
*A61L 24/02* (2006.01)
*A61L 24/04* (2006.01)
*A61L 24/06* (2006.01)
*A61L 24/08* (2006.01)

(52) U.S. Cl.
CPC ........ *A61L 24/108* (2013.01); *A61K 49/0438* (2013.01); *A61L 24/0031* (2013.01); *A61L 24/02* (2013.01); *A61L 24/043* (2013.01); *A61L 24/06* (2013.01); *A61L 24/08* (2013.01); *A61P 7/04* (2018.01); *A61L 2300/418* (2013.01)

(58) Field of Classification Search
None
See application file for complete search history.

(56) References Cited

U.S. PATENT DOCUMENTS

| | | | |
|---|---|---|---|
| 5,202,352 A | 4/1993 | Okada et al. | |
| 5,624,685 A | 4/1997 | Takahashi et al. | |
| 5,695,480 A | 12/1997 | Evans et al. | |
| 8,491,623 B2 * | 7/2013 | Vogel | A61B 17/12131 606/108 |
| 9,132,087 B2 * | 9/2015 | Lichter | A61K 47/32 |
| 2008/0208163 A1 * | 8/2008 | Wilkie | A61L 31/14 604/506 |
| 2008/0215036 A1 | 9/2008 | Vogel et al. | |
| 2017/0043050 A1 | 2/2017 | Vogel et al. | |

FOREIGN PATENT DOCUMENTS

| | | |
|---|---|---|
| JP | 4-197359 A | 7/1992 |
| JP | 05-103802 A | 4/1993 |
| JP | 05-208917 A | 8/1993 |
| JP | 2000-517298 A | 12/2000 |
| JP | 2001-039869 A | 2/2001 |
| JP | 2002-256075 A | 9/2002 |
| JP | 2007-271388 A | 10/2007 |
| JP | 2010-512230 A | 4/2010 |
| JP | 6047689 B1 | 12/2016 |
| WO | 2005/058384 A2 | 6/2005 |
| WO | 2016/153072 A1 | 9/2016 |

OTHER PUBLICATIONS

Huang et al (Thermo-sensitive composite hydrogels based on poloxamer 407 and alginate and their therapeutic effect in embolization in rabbit VX2 liver tumors. Oncotarget. 2016; 7:73280-73291) (Year: 2016).*

Garner et al (Chemically Modified Natural Polysaccharides to Form Gels. Springer International Publishing Switzerland 2014. pp. 1-25) (Year: 2014).*

Lili Huang et al., "Thermo-sensitive composite hydrogels based on poloxamer 407 and alginate and their therapeutic effect in embolization in rabbit VX2 liver tumors," Oncotarget, 2016, pp. 73280-73291, vol. 7, No. 45.

Timothy A. Becker et al., "Calcium alginate gel: A biocompatible and mechanically stable polymer for endovascular embolization," Journal of Biomedical Materials Research, 2001, pp. 76-86, vol. 54.

Timothy A. Becker et al., "Flow properties of liquid calcium alginate polymer injected through medical microcatheters for endovascular embolization," Journal of Biomedical Materials Research, 2002, pp. 533-540, vol. 61.

Jean Raymond et al., "Alginate for Endovascular Treatment of Aneurysms and Local Growth Factor Delivery," AJNR Am J Neuroradiol, Jun./Jul. 2003, pp. 1214-1221, vol. 24.

Hyun Mee Lee et al., "A gel-forming poly-L-guluronic acid produced from no guluronate-rich marine algae using new hydrolysis method: test for endovascular embolization," J Mater Sci: Mater Med, 2009, pp. 1917-1926, vol. 20.

(Continued)

*Primary Examiner* — Jake M Vu
(74) *Attorney, Agent, or Firm* — Sughrue Mion, PLLC

(57) ABSTRACT

Provided is a liquid embolic agent composition capable of solving problems of conventional embolic agents, which can be used in a treatment of a vascular disease such as cerebral aneurysm. The problems are solved by a liquid embolic agent composition characterized in containing a hydrogel forming component having a calcium ion entrapping ability, and an anti-biodegradation component. The hydrogel forming component having a calcium ion entrapping ability is at least one kind of acidic polysaccharide selected from the group consisting of alginate, gellan gum, carrageenan, and carboxymethyl cellulose salt; and the anti-biodegradation component is at least one kind selected from the group consisting of hydroxypropyl methylcellulose, methylcellulose, polyvinyl alcohol, polyallylamine, poly-N-vinyl acetamide, and cellulose acetate.

12 Claims, 3 Drawing Sheets

(56) References Cited

OTHER PUBLICATIONS

Japanese Decision to Grant a Patent issued in JP 2018-528812 dated Jul. 17, 2018.
Written Opinion of the International Searching Authority of PCT/JP2018/006147 dated Apr. 10, 2018.
International Search Report of PCT/JP2018/006147 dated Apr. 10, 2018.
Extended European Search Report, dated Feb. 17, 2021, issued by the European Patent Office in European Patent Application No. 18906988.3.

* cited by examiner

LIQUID EMBOLIC AGENT COMPOSITION

CROSS REFERENCE TO RELATED APPLICATIONS

This application is a National Stage of International Application No. PCT/JP2018/006147, filed Feb. 21, 2018.

TECHNICAL FIELD

The present invention is directed to a liquid embolic agent composition and relates to a liquid embolic agent composition that can be used for treatment of cerebrovascular diseases, such as cerebral aneurysm.

BACKGROUND ART

For the endovascular treatment of cerebrovascular diseases, various types of embolic materials, such as metallic coils and liquid embolic materials, are used to occlude abnormal blood vessels (Patent Literature 1). The limitations of the currently used various types of embolic materials are described in Patent Literature 2. Patent Literature 2 describes a technology that uses an active ingredient protein produced by an aquatic insect and utilizes properties derived from the proteinaceous composition, i.e. E2P, which includes two types of protein molecular species, in order to improve the multiple limitations of commercially available products.

In the technique described in Patent Literature 2, items (1) to (5), derived from the properties of the active ingredient, E2P, remain as limitations to be fixed. (1) In the previously performed animal experiments, E2P formed powdery substances rather than forming a solid mass when injected into a target blood vessel. (2) Availability of E2P depends on the seasons due to the life cycle of the organism that produces the raw materials. (3) E2P is a pure protein composition that can be biologically decomposed and absorbed, and, as a result, there is a possibility that the embolization performance is not satisfactorily retained for long-term occlusion of blood vessels. (4) Since E2P is a novel compound, there is a necessity for demonstrations of nontoxicity toward biological organs, as required for FDA approval. (5) There is no information about functional reliabilities of E2P as an active ingredient, i.e., when E2P is injected and deployed into blood vessels, the maximal tolerable blood pressure is unknown. There is no device to measure the maximal tolerable pressure.

The property of item (1) causes a problem that, during deployment in a brain blood vessel, the powdered E2P can migrate into distal untargeted vessels, reducing the embolic efficiency per injected volume of the E2P solution. For item (2), which also relates to item (5), through subsequent researches by the inventors of the present application (Non-Patent Literatures and 2), the resource organism was found to actively biosynthesize the active ingredient proteins in E2P in the larval stage, a period only from early summer to early autumn. The resource organism, then, suspends the biosynthesis of E2P, as the river water temperature is lowered in the winter season. For item (5), there is a possibility that a normalized degree of phosphorylation, which is an indicator of aggregation performance of E2P, is potentially influenced upon seasonal fluctuations throughout the life cycle of the resource organism, suggesting that item (5) can therefore still be attributed to a lack of scientific evidence.

CITATION LIST

Patent Literature

PATENT LITERATURE 1: JP H5-103802 A
PATENT LITERATURE 2: JP 6047689 B

Non-Patent Literature

NON-PATENT LITERATURE 1: Bai, X., et al., Molecular cloning, gene expression analysis, and recombinant protein expression of novel silk proteins from larvae of a retreat-maker caddisfly, Stenopsyche marmorata. Biochemical and Biophysical Research Communications, 2015. 464 (3): p. 814-819.

NON-PATENT LITERATURE 2: Nomura, T., et al., Characterization of silk gland ribosomes from a bivoltine caddisfly, Stenopsyche marmorata: translational suppression of a silk protein in cold conditions, Biochemical and Biophysical Research Communications, 2016. 469 (2): p. 210-215.

SUMMARY OF INVENTION

Technical Problems

The present invention has been achieved in view of problems (1) to (5) above, and an object of the present invention is to solve these problems by providing novel liquid embolic agent compositions.

Solutions to the Problems

According to the liquid embolic agent compositions of the present invention, the problems are solved by involvements of a hydrogel-forming component having an inherent ability for entrapping calcium ions, and a component that is resistant to biodegradation.

Here, the hydrogel-forming component is preferred to be an acidic polysaccharide, such that there is an inherent ability for entrapping calcium ions.

Here, the acidic polysaccharide is preferred to be at least one kind selected from a group consisting of alginates, gellan gums, carrageenans, and carboxymethyl cellulose salts.

Here, the acidic polysaccharides are preferred to be sodium alginates and gellan gums.

Here, the component resistant to biodegradation is preferred to be at least one kind selected from a group consisting of hydroxypropyl methylcelluloses, methylcelluloses, polyvinyl alcohols, polyallylamines, poly-N-vinyl acetamides, and cellulose acetates.

Here, a coagulation-promoting component is preferred to be additionally contained, and the coagulation-promoting component is at least one kind selected from a group consisting of colloidal silicas, poly(N,N-dimethyl) acrylamides, enzyme preparations for food processing, poly-L-lysine hydrobromides, poly-L-glutamic acid-sodium salts, chitosans, and silk fibroins.

Here, the composition is preferred to be a liquid in vitro and gelates in vivo, expressing a bioadhesiveness.

Here, the composition is preferred to be used in the treatment of cerebral aneurysm.

Here, the composition further is preferred to contain an iodine type angiographic contrast agent.

Advantageous Effects of the Invention

The liquid embolic agent compositions of the present invention are biocompatible, inert to human bodies, and have a function of embolizing an abnormal portion of a blood vessel by reacting with blood to form gels. The liquid embolic agent compositions can be used in the therapeutic embolization of a feeding blood vessel for cerebral aneurysm, cerebral arteriovenous malformation, dural arteriovenous fistula, and brain tumor, or in an embolization of a parent blood vessel of nasal bleeding. In addition, the liquid embolic agent compositions of the present invention can be efficiently and widely applied to treatments of hysteromyoma, liver cancer (embolization therapy), vascular occlusion upon multiple trauma, and the like.

DESCRIPTION OF EMBODIMENTS

Figure 1:
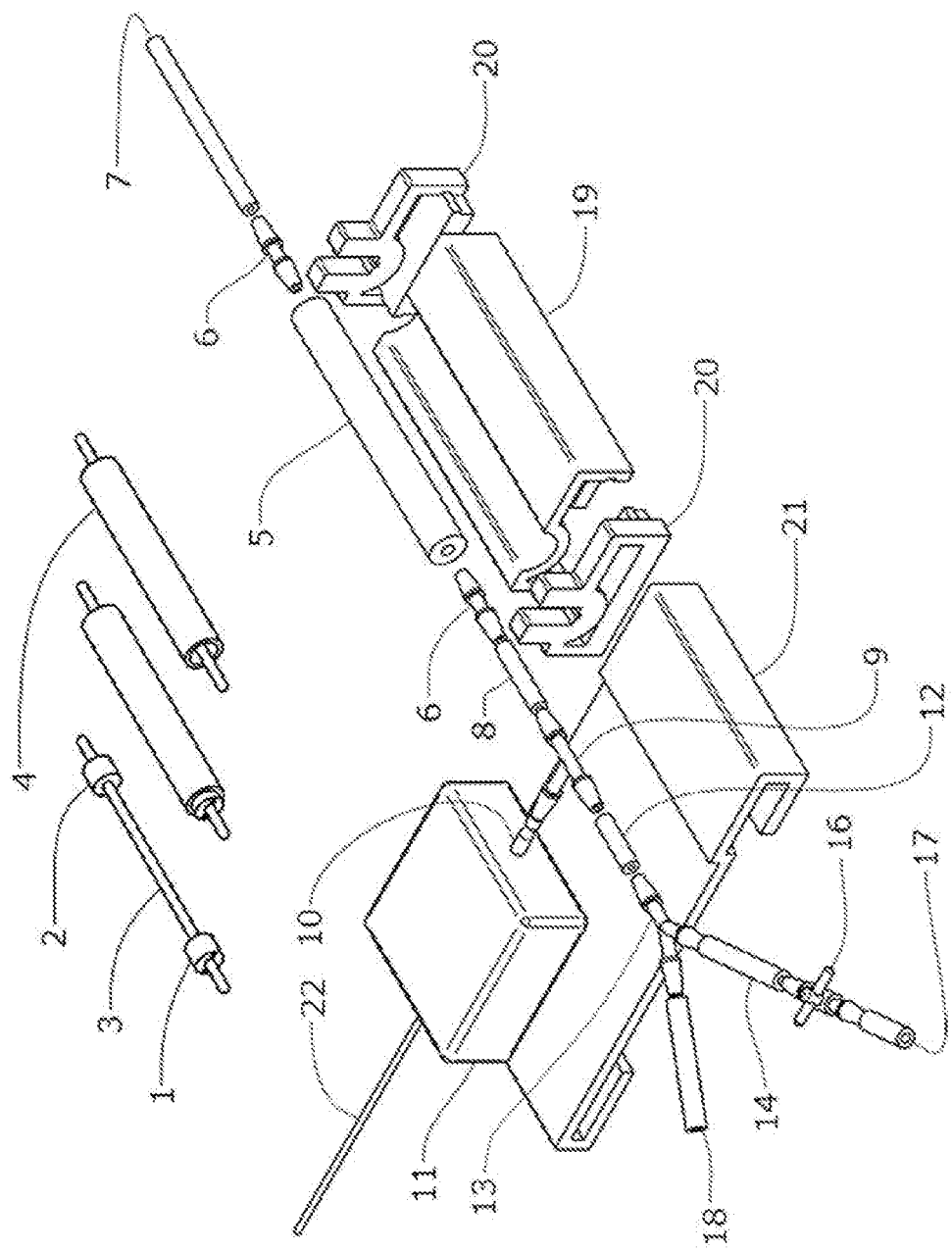
FIG. 1 schematically shows an apparatus for producing a gel tube as a blood vessel model and an apparatus for evaluating the maximal tolerable pressure of the liquid embolization compositions in the present invention.

Hereinbelow, a liquid embolic agent composition, according to one embodiment of the present invention (hereinbelow referred to as present embodiment), will be described.

The problems (1) to (4) in the prior art can be solved by improving material aspects. A composition involving the embolic components is created that instantly reacts with substances in the blood and that turns into a hydrogel-like substance. The components are preferred to exhibit a slow biodegradation rate, otherwise are not responsible for any potential biodegradations, are commercially available, and have already been approved by government authorities for utilization as food additives, etc. The composition may involve a single compound or a combination of different compounds for the sake of fixing the problems (1) to (4). Further, since the liquid embolic agent compositions are preferably injected into a blood vessel from the tip of a microcatheter, the compositions are capable of passing through a catheter with an inner diameter of approximately 0.6 mm, without the operator causing an uncomfortable resistance. Further, the liquid embolic agent compositions delivered from microcatheters are preferred to exert the desired performance in the presence of an angiographic contrast agent and, more preferably, function to retain contrast compounds inside the coagulated composition, thereby preventing diffusion into the blood.

A substance that satisfies the requirements for solving problems (1) to (4) should have a property of reacting with intrinsic components in the blood. In the case of E2P, phosphoserine residues in the active ingredient protein molecules thereof react with calcium ions in the blood, causing instant aggregation. Therefore, the compositions preferably involve certain components that are capable of reacting with intrinsic calcium ions in the blood. If such a component has a property of reacting with a substance in blood other than calcium ions (hereinbelow referred to as M), for example, under assumable cases where the M concentration drops to zero depending on a given condition inside a human body, then, in such a physiological state, only E2P will coagulate, meaning that the problems will not be eliminated or reduced. Generally, during surgical procedures, real-time monitoring is not performed on the M concentration, the pH value, and the levels of intrinsic/targeted chemicals in the blood. Operators decide treatment strategies based on angiographic findings, along with heart rates and blood pressure values. On the other hand, the calcium-ion concentrations in blood are maintained at a range from 2 to 5 mM, which allows both E2P and the liquid embolic agent compositions of the present invention to coagulate together in a coordinated function while demonstrating their embolization performances.

The substances, which satisfy the improvement requirements derived from problems (1) to (4), have been tried, and, after trials, errors, and ingenuities, the substances listed in Table 1 have been exploited (in Table 1, range of blending amount (wt %) represents the weight percentages in total mass of the liquid embolic agent composition as 100 wt % (equal to mass %). The numbers (1) to (4), which are indicated in the column of "Problems to be reduced/solved" in Table 1, correspond to the problems (1) to (4). The substances listed in the column "Components in composition" have single or multiple functions and roles, which are described as "calcium ion entrapping", "hydrogel formation", "resistant to biodegradation", and "coagulation promoting". For all of the components in Table 1, water and buffer solutions that are isotonic to body fluids can be used as solvents for preparing the liquid embolic agent compositions, and in any mixtures of their aqueous solutions the components will not instantly coagulate to precipitate before injection. The components listed in Table 1 are injectable into blood vessels from a microcatheter and, thus, satisfy a physical performance required as a liquid embolic substance.

TABLE 1

| Components in composition | Functions and roles in embolic agent composition | Problems to be solved | Range of blending amount (wt %) |
|---|---|---|---|
| Sodium alginate | Calcium ion entrapping, hydrogel formation | (1) (2) | 0.5-2.0 |
| Gellan gum | Calcium ion entrapping, hydrogel formation | (1) (2) | 0.1-0.5 |
| Carrageenan | Calcium ion entrapping, hydrogel formation | (1) (2) | 0.2-1.0 |
| Carboxymethyl cellulose salt | Calcium ion entrapping, hydrogel formation, resistant to biodegradation | (1) (2) (3) | 0.1-1.0 |
| Hydroxypropyl cellulose | resistant to biodegradation | (1) (2) (3) (4) | 0.1-5.0 |
| Methylcellulose | resistant to biodegradation | (1) (2) (3) (4) | 0.1-4.0 |
| Polyvinyl alcohol | resistant to biodegradation | (1) (2) (3) (4) | 0.1-8.0 |
| Sodium caseinate | Calcium ion entrapping, Coagulation promoting | (2) (4) | 0.1-10.0 |
| Gelatin | hydrogel formation | (1) (2) (4) | 0.1-5.0 |
| Polyacrylic acid | Calcium ion entrapping, Coagulation promoting | (1) (2) (3) (4) | 0.1-1.0 |

TABLE 1-continued

| Components in composition | Functions and roles in embolic agent composition | Problems to be solved | Range of blending amount (wt %) |
|---|---|---|---|
| Chitosan beads | Calcium ion entrapping, Coagulation promoting | (1) (2) | 0.5-5.0 |
| Colloidal silica particles | Coagulation promoting | (3) | 0.5-2.0 |
| Poly(N,N-dimethyl) acrylamide | Coagulation promoting | (3) | 0.1-5.0 |
| Enzyme preparation for food processing | Coagulation promoting | (1) (2) (4) | 1.0-10.0 |
| Casein, from bovine milk | Calcium ion entrapping, Coagulation promoting | (2) (4) | 1.0-2.0 |
| Polyallylamine | resistant to biodegradation | (2) (3) | 0.5-5.0 |
| Poly-N-vinyl acetamide | resistant to biodegradation | (2) (3) | 1.0-10.0 |
| Agar | hydrogel formation | (1) (2) (4) | 0.1-3.0 |
| Poly-L-lysine hydrobromide | Coagulation promoting | (2) (4) | 1.0-5.0 |
| Poly-L-glutamic acid-sodium salt | Coagulation promoting | (2) (4) | 1.0-5.0 |
| Chitosan | Coagulation promoting | (1) (2) | 0.1-0.5 |
| Cellulose acetate | resistant to biodegradation | (2) (3) | 0.1-0.2 |
| Blue dextran | resistant to biodegradation, visualization with Blue color | (3) | 0.5-2.0 |
| Silk fibroin | Coagulation promoting | (1) (2) | 1.0-4.0 |
| Phosphorylated Silk fibroin | Calcium ion entrapping, Coagulation promoting | (1) (2) | 1.0-8.0 |
| E2P | Calcium ion entrapping, Coagulation promoting | — | 0.1-2.0 |

Most of the components in the compositions listed in Table 1 are commercially available as reagent-grade chemicals, as well as food additives or ingredients. Although the components in the compositions are varied in their purities, molecular weight distributions, and so on, they are able to exert their performances as described in the present invention; that is, the coagulation properties are potentially ensured at the calcium-ion concentrations in the blood. Among the polymer compounds listed in Table 1, sodium alginate, gellan gum, carrageenan, and carboxymethyl cellulose sodium salt are classified as acidic polysaccharides. Carboxymethyl cellulose sodium salt, hydroxypropyl cellulose, and methylcellulose are chemically modified forms of cellulose, a poorly water-soluble natural polysaccharide. The chemically modified celluloses are not decomposed or absorbed via metabolic pathways in vivo and are, therefore, resistant to biodegradation, serving the anti-biodegradability role in the embolic agent compositions.

The acidic polysaccharides undergo hydrogelation in the presence of calcium ions and, thus, are safe substances to be used as food additives, particularly as thickening polysaccharides. The compositions that include any of these acidic polysaccharides at appropriate ratios exhibit various coagulation behaviors when injected into an artificial serum. Although polyvinyl alcohol (PVA) and hydroxypropyl cellulose (HPC) in Table 1 are not components that undergo gelation with calcium ions, both polymers can be used as a food additive and are not metabolized in the human bodies. Therefore, these polymers are not affected by the biodegradation process during deposition in the human blood. Thus, these components are used to guarantee long-term mechanical durability and stability after deployment in blood vessels. Each of the liquid embolic components listed in Table 1 has ideal properties for utilization as a cerebrovascular embolic substance. In the "Examples" section, preparation procedures for the compositions are described, as well as the efficacy of the materials included in the present invention.

Both casein from bovine milk and sodium caseinate in Table 1 have calcium ion-entrapping abilities, but tend to coagulate in disordered geometries as powders or small amorphous particles; therefore, in order to solve problem (1), use of an acidic polysaccharide is preferable compared with acidic proteins, such as the caseins. In cases where the components of a liquid embolic agent composition are positively charged basic polymer compounds in Table 1 (i.e., chitosan, polyallylamine, and poly-L-lysine hydrobromide) that coexist with an acidic polysaccharide as an active ingredient, the acidic polysaccharides and the basic polymers form a complex due to electrostatic interactions. Since the complexation occurs even in the absence of coexisting calcium ions, an appropriate amount of the basic polymer compounds can reinforce the cohesion between acidic polysaccharide molecules when the hydrogelation occurs upon the entrapment of calcium ions by the acidic polysaccharides.

In cases where the relative concentration of the basic polymer compound is excess in the liquid embolic agent composition, however, the electrostatic interaction induces a spontaneous coagulation, resulting in precipitation in the absence of supplied calcium ions. This phenomenon impairs the efficacy of the acidic polysaccharide as a component of the liquid embolic agent composition in the present invention, i.e., the function of the basic polymer compound within the embolic agent to react with calcium ions and form hydrogels is impaired. Therefore, as components of the liquid embolic agent composition in the present invention, the blending ratios between the acidic polysaccharides and the basic polymer compounds are important; the basic polymer compound provides the coagulation-promoting function, and, as a result of trials and errors, ranges of blending ratios have been found, as described in Table 1.

<Liquid Embolic Agent Composition>

The term "liquid embolic agent composition" according to the present embodiment refers to a composition, which is a liquid in vitro that undergoes gelation with expressing bioadhesive actions in vivo; and the term is synonymous with liquid embolic composition, liquid embolus composition, and liquid embolus forming composition.

The liquid embolic agent composition according to the present embodiment contains a hydrogel-forming component having a calcium ion-entrapping ability, an anti-biodegradable component, a coagulation promoting component, and other additional components.

(Hydrogel-Forming Components)

From the components shown in Table 1, for example, the acidic polysaccharides can be used as the hydrogel-forming components and have a calcium ion-entrapping ability. As acidic polysaccharides, they can be used either as a single component or as a combination of multiple components selected from the list consisting of alginate, gellan gum, carrageenan, and carboxymethyl cellulose salt. As acidic polysaccharides, use of a combination of sodium alginate and gellan gum is preferable. The blending ratios of the hydrogel-forming components in the liquid embolic agent compositions are not particularly restricted. In general, the calcium-ion concentrations in the blood of homeothermic animals, for instances, humans, horses, and pigs, varies from 2.5 to 4.0 mM, and, in correspondence with these calcium concentration ranges, each of the components may be used with the blending ratios described in Table 1.

(Anti-Biodegradable Components)

As the anti-biodegradable component, as listed in Table 1, at least one kind from the group consisting of hydroxypropyl methylcellulose, methylcellulose, polyvinyl alcohol, polyallylamine, poly-N-vinyl acetamide, and cellulose acetate, or a combination of polymers from this group, is possible for use. The blending ratios of the anti-biodegradable components in the liquid embolic agent compositions are not particularly restricted if the embolization performance is satisfactory, and the components may be used within the range of the blending ratios in Table 1, as described above.

(Coagulation-Promoting Components)

From the coagulation-promoting components, as given in Table 1, at least one kind from the group consisting of colloidal silica, poly(N,N-dimethyl) acrylamide, enzyme preparations for food processing, poly-L-lysine hydrobromide, poly-L-glutamic acid-sodium salt, chitosan, silk fibroin, or a combination of components from this group, is possible for selection. Blending ratios of the coagulation-promoting components in the liquid embolic agent compositions are not particularly restricted if the embolization performances are satisfactory, and the components may be used within the range of the blending ratios in Table 1, as described above.

(Buffer Solutions Isotonic to Body Fluid)

The liquid embolic agent compositions according to the present embodiments are prepared by appropriately selecting each of the components and then dissolved in a buffer solution, which is isotonic to a body fluid. The liquid embolic agent composition thus prepared is then injected through a catheter into a target blood vessel (the blood flow in the target site) to be occluded. Upon injection from the catheter tip into the target blood vessel, the composition instantaneously coagulates to ensure embolization of the targeted site. Commonly used buffering compounds can be applied to the isotonic buffer solutions in the present invention. Applicable buffer solutions are, for example, Tris HCl, HCl—KCl, organic acids and their sodium or potassium salts (e.g., acetic acid-sodium acetate, boric acid-sodium borate, phthalic acid-potassium phthalate, etc.), organic base-inorganic acid salts (e.g., glycine-HCl, imidazole-HCl, etc.), components that are capable of providing a buffering action, (e.g., HEPES and MOPS), and neutral inorganic salts (e.g., NaCl, KCl, and CsCl). These may be selected and used based upon biocompatibility and safety in the human body.

The following Examples employ aqueous solutions containing 0.15 mol/L sodium chloride, 20 mmol/L tris(hydroxymethyl)aminomethane hydrochloride (pH 8.0), or 5.0 mmol/L calcium chloride, as isotonic aqueous buffer solutions that reconstitute the osmotic pressure approximately equal to that of human plasma.

(Other Components)

The liquid embolic agent composition according to the present embodiments also comprises other components for medical purposes, including a diagnostic reagent and a therapeutic agent, which will not impair the performance of the liquid embolic agent. As diagnostic reagents, angiographic contrast agents can be involved; use of iodine type angiographic contrast agents, which are commercially available as aqueous solutions, are preferred for being capable of preserving the dissolution state of each component contained in the liquid embolic agent compositions.

(Application)

The liquid embolic agent compositions according to the present embodiments are liquids in vitro and coagulate to form hydrogels by reacting with blood to exhibit a bioadhesiveness in vivo and, therefore, are used to occlude the abnormal portions of given blood vessels. The liquid embolic agent compositions can be used in a treatment of cerebral aneurysm, but application aspects of the compositions are not restricted thereto. For intracranial lesions, cerebral arteriovenous malformation, dural arteriovenous fistula, and aneurysms, the compositions can be used to occlude them, as well as for a feeding blood vessel to the brain tumor and a parent blood vessel in a nasal bleeding. For extra-cranial lesions, the liquid embolic agent compositions of the present invention can be efficiently and widely applied for the treatment of uterine fibroid and liver cancer (embolization therapy), for the vascular occlusions upon multiple trauma, and the like, as well as other advanced therapies or preventions in the medical field.

In the present embodiment, the liquid embolic agent compositions according to the present invention have been described. The descriptions in this embodiment, however, are merely some examples to facilitate understanding of the present invention and do not restrict the present invention. As a matter of course, the present invention can be changed or improved without departing from the core of the invention thereof, and the present invention includes an equivalent thereof.

Example

Hereinbelow, specific examples will be described with regards to the liquid embolic agent compositions of the present invention, but the present invention is not limited thereto.

Example 1

A liquid embolic agent composition was prepared by mixing sodium alginate (Alg), gellan gum (Geln), and HPC together with the individual ranges of weight percent concentrations shown in Table 1. The liquid embolic agent composition was loaded into a syringe that was connected to a microcatheter. The liquid embolic agent composition was delivered through the microcatheter lumen and injected via the distal tip into artificial serum containing 2 mM calcium chloride, 150 mM sodium chloride, and 20 mM tris buffer solution (pH 8.0). As soon as the composition was exposed to the artificial serum, the Alg and Geln reacted with calcium ions in the solution, and the composition immediately coagulated to form a filamentous hydrogel. This filamentous hydrogel was not broken off while the injection was continued until the liquid composition in the syringe was running out, and the hydrogel was detached from the microcatheter tip upon releasing the injection pressure, i.e., the pushing force.

Example 2

To determine the impact of percentages of Alg and Geln in Example 1, a liquid embolic agent composition in which the Alg content was higher than 2.0 wt %, was prepared and the same procedure was performed. As a result, the shape of a hydrogel, formed by reaction with calcium ions, became spherical rather than filamentous in form. Upon continuous injection of the liquid embolic agent composition from a syringe, the size of the spherical hydrogel enlarged as if a balloon bulged on the catheter tip. The spherical hydrogel was detached from the tip of the microcatheter just by releasing the injection pressure and pulling the tip of the microcatheter from the delivered material. The similar change in shape from the filamentous hydrogel to the spherical hydrogel was observed not only by increasing the Alg content, but also by diluting the composition with water by about two times.

A liquid embolic agent composition containing the substances described in Table 1 behaves like coil devices used for the treatment of the cerebral aneurysms when the composition forms a filamentous hydrogel shape upon exposure to calcium ions. When the hydrogel is spherical, the composition can also behave like the other liquid embolic agents described in Patent Literature 2. Both the filamentous and spherical hydrogels, which were formed from the embolic agent composition containing the components described in Table 1, were suitable for an injection via a microcatheter into a blood vessel, for an embolization procedure, for delivery as an embolic substance, and for a catheter removal procedure. These physical properties and conditions provided by the liquid embolic agent compositions according to the present invention are efficacious and beneficial for the operators and meet the criteria to solve the problems related to E2P, in addition to the problems described in Patent Literature 2.

Example 3

In Example 3, the functional effectiveness of the liquid embolic agent compositions according to the present invention were evaluated by using a silicone model that simulates the shapes of cerebral aneurysms and blood vessels. These models are commonly used for the purpose of operators mastering the microcatheter technique.

An artificial serum, which has the same composition described in Example 1, was circulated in a silicone aneurysm model used for aneurysm treatment training (hereinbelow referred to as cerebral aneurysm model) at a pumping rate equal to the blood flow inside a brain blood vessel of the human body. The liquid embolic agent composition described in Example 1 was then diluted with a commercially available iodine-type angiographic contrast agent. Because the iodine-type angiographic contrast agent was an aqueous solution, each component contained in the liquid embolic agent composition remained in a dissolved state. The liquid embolic agent composition containing the contrast agent was loaded into a syringe, and a microcatheter was connected. The tip of the microcatheter was advanced and placed in the cerebral aneurysm model. The liquid embolic agent composition was injected from the tip of the microcatheter into the model aneurysm cavity, the composition coagulated in the form of the spherical hydrogel due to the dilution with the contrast agent solution and bulged to entirely fill the physical shape of the aneurysm cavity.

Observations made during above procedures with an angiography machine revealed that the liquid embolic agent composition, which acquired radiopacity due to the coexistence of the contrast agent, was continuously injected, keeping its spherical shape until the intra-aneurysmal cavity was filled. At the same time, the images obtained under angiographic observation demonstrated that the physical shape of the injected and coagulated liquid embolic agent composition was neither deformed into pieces nor fragmented by the hydrodynamic stress generated by the circulating flow of the artificial serum. This property exhibited by the liquid embolic agent composition satisfies the requirement that "the embolic substances do not migrate into a distal blood vessel". The non-adherence of the tip of the microcatheter to the coagulated liquid embolic agent composition was also advantageous, and the microcatheter was pulled out from the aneurysm cavity without resistance.

Summary of Examples 1 to 3

Examples 1 to 3 above indicate that the liquid embolic agent compositions according to the present invention have ideal properties and characteristics when utilized as embolic agents. There are a variety of cerebrovascular diseases, including not only the cerebral aneurysm described above, but also cerebral arteriovenous malformation (AVM), in which relatively thin/small arteries and veins become abnormally entangled. Especially for the treatment of AVM, liquid embolic agents are effective as compared to coil shaped devices. However, commercially available cyanoacrylate-type embolic substances have an excessively strong adhesion force and, therefore, often cause catheter entrapment when the catheter is withdrawn from the vessels. Onyx liquid embolic system, another commercially available product, must be injected in the presence of an organic solvent, dimethylsulfoxide (DMSO), together with tantalum type particles as the angiographic contrast compound, and, consequently, the patient's cerebral blood vessels are exposed to chemical substances upon treatment. The liquid embolic agent composition according to the present invention solves these problems associated with the conventional embolic substances.

Example 4

A physical form of AVM found in the human brain can be simulated using a surgically created animal model composed of the host animal's blood vessels with appropriate diameters for these purposes. The AVM silicone models, similar to those used in Example 3, do not exist as commercially available products. Therefore, to evaluate the efficacy of the liquid embolic agent compositions according to the present invention, as an example, cerebral vessels in a rat were used.

A microcatheter was inserted from a femoral artery of the rat and advanced to a brain blood vessel, and the tip of the microcatheter was placed in the left side internal carotid artery. A contrast medium was injected from this location (X1) to obtain a three-dimensional structure image of the entire cerebrovascular network. The tip of the microcatheter was then advanced toward the middle cerebral artery, and, from this location (X2), the liquid embolic agent composition according to the present invention without contrast medium was injected. Thereafter, the catheter tip was withdrawn to the location X1, and the contrast medium was injected again to confirm occlusion of the target vessel. As a result, the vascular network in the left side of the brain was not visualized after the injection of the liquid embolic agent composition. This confirmed that the blood flow in the un-visualized brain vessels were blocked with the coagulated liquid embolic agent composition.

Example 5 Production of Gel Tubes

As shown in the Examples 1 to 4, the embolic agent compositions according to the present invention are able to occlude the silicone vessel model and the animal model that uses the cerebrovascular network in a rat. One of the problems to be solved by the present invention was (5), the maximal tolerant pressure of the occluded vessel after treatment with E2P is not clear, and there is no appropriate device to evaluate the value. Therefore, an experimental system was constructed using artificial serum, and the detailed results thereof are described below.

Usually animal blood vessels are not easily available, and, in most cases, the vessels from laboratory animals, e.g. rat or others, are used in experiments. However, even among the same species, each animal has individual differences in the physical shapes of the animal blood vessels, including wall thicknesses, lengths, and diameters, that makes reproducibility of experimental conditions difficult. Consequently, a large number of animal experiments would be required for the quantification of maximal tolerance pressure of the occluded vessels treated with the liquid embolic agent compositions according to the present invention. Therefore, as an alternative method, an in vitro model system that represents an animal blood vessel was established and used to evaluate the maximal tolerant pressure of the occluded vessels with the liquid embolic agent compositions according to the present invention.

As an alternative to an animal blood vessel, material compositions were investigated for creating gel tubes that reconstitute the chemical characteristics of the inner surfaces and the mechanical properties of real vessels. The upper part of FIG. 1 represents an apparatus for gel tube production.

The apparatus shown in the upper part of FIG. 1 is composed of two silicone rubber stoppers 1 and 2, an acrylic rod 3 that has a thickness of 2 mm and that coaxially penetrates through the silicone rubber stoppers' cross-sections, and a glass tube 4 that has an inner diameter of 8 mm and fixes these members in the coaxial direction. The silicone rubber stopper 1 has two pores, one pore is an insertion port for an injection needle for pouring a gel solution inside, and the other pore is for air venting at the time of gel solution injection.

Table 2 shows a composition of the gel solution. As shown in Table 2, the gel solution is composed of three monomers as major components, acrylamide (AA), dimethylacrylamide (DMA), and methylenebisacrylamide (MBA). Although AA, DMA and MBA are publicly known compounds, the composition ranges described in Table 2 have been discovered to be optimal for producing gel tubes as blood vessel models according to the present invention. Concentration ratios of AA having a hydrophilic group and DMA having a hydrophobic group are of importance since these factors influence an appropriate water retention ratio inside the gel and hydrophilicity to the gel surface.

TABLE 2

| Gel solution components | Ranges of blending amount (per 25 mL) |
|---|---|
| Acrylamide | 4.0-6.5 g |
| N,N-dimethylacrylamide | 0.5-0.8 mL |
| N,N'-methylenebisacrylamide | 0.1-0.5 g |
| Sodium chondroitin sulfate | 0.05-0.4 g |
| Albumin (Serum-, Egg white-derived, etc.) | 0.05-0.2 g |
| Polyvinyl alcohol | 0.05-0.4 g |

In addition to these fundamental components, sodium chondroitin sulfate (SCS) and protein albumin provide the organic chemical properties of various polymeric compounds present on the surface of vascular endothelial cells. Reagent-grade albumins are commercially available, and those derived from egg white or serum can be used. SCS is a sulfated polysaccharide that can bring hydroxyl groups to the gel surface. Albumins are proteins, which not only provide various functional groups derived from amino acid side chains thereof, but also impart mechanical elasticity to the gel tube in association with thermal denaturation upon exothermic gelation. This action of albumin not only improves the strength of the gel tube, but also imparts an elasticity similar to that of a blood vessel, i.e., the model system is able to absorb blood pressure. Gel tubes in the absence of ovalbumin were less elastic and more easily cracked to be broken, as compared with those in the presence of ovalbumin.

In addition to the above gel solution composition for the experimental system of the present invention, other water-soluble, polymeric compounds can be involved in the gel solution. For example, a polyvinyl alcohol (PVA) preparation or HPC with higher molecular weights than that of SCS can be added. As a polyol model of oligosaccharides present on the vascular endothelial cell surfaces, PVA and HPC also are effective at attracting water molecules to the gel surface.

Ammonium persulfate (APS) solution was added to the gel solution that contains the above fundamental and additional component mixture, a needle tip connected to a syringe was inserted into a pore of the silicon rubber stopper 1, and the gel solution thus prepared was injected into the apparatus of the upper part of FIG. 1. Polymerization of the monomer molecules in the injected solution was initiated by the action of APS, and a gel tube was formed, filling a space formed by the acrylic rod 3 and the inner wall of the glass tube 4, i.e., a tubular space. A gel tube thus prepared was removed from the apparatus and used in evaluation of the maximal tolerant pressures of the deployed embolic compositions.

For evaluation of the maximal tolerant pressure of the deployed embolic composition, the apparatus as shown in FIG. 1 was designed and constructed. As shown in the lower part of FIG. 1, the apparatus for evaluating the maximal tolerant pressure of the deployed embolic composition is composed of a blood vessel model 5, a gel tube produced using the gel tube preparation apparatus and via the gel tube preparation procedure described above; a polypropylene connector 6 as a joint between the blood vessel model 5 and a flow path system piping; a silicone tube piping 7 in the drain direction; a short silicon tube piping 8 in the sensor direction; a polypropylene T-type stay 9 connected to the silicon tube piping 8; a fluid pressure sensor input 10 that is seal-connected to the direction of the trunk of the T-type stay 9 by using a silicone tube; a sensor circuit case 11 that stores a small electronic circuit board, including a fluid pressure sensor and an instrumentation amplifier; a silicon tube piping 12 for connection of the T-type stay 9 to the pump direction, a three-branched polypropylene connector 13 connected ahead thereof; a silicon tube piping 14 for connection of the connector 13 to the direction of microcatheter insertion; a small valve 16; a silicon tube piping 17 for microcatheter insertion; and a silicone tube piping 18 for perfusing a simulated serum fed from the pump into the apparatus.

Both ends of blood vessel model 5 (gel tube 5) are composed of a combination of left- and right-side units 20 capable of locking the connectors 6 inside the longitudinal groove and a gel tube holder 19 having a shape engaging with bottom portions of the side units; therefore, the gel tubes 5 and 6 are physically fixed. For this structure, during a perfusion of the simulated serum under a pressure loading condition of 400 mmHg or less, the pressure value can be propagated to the fluid pressure sensor input 10, without a detachment of the connector 6 from the gel tube 5 or a pressure loss from the joints of them. The fluid pressure sensor input 10 and the sensor circuit case 11 are fixed on a sensor stage 21 for adjusting the gap with the gel tube holder 19 in the height direction; hence, the dead space in between the piping systems is minimized. A value measured by the fluid pressure sensor is transmitted in real time to a microcomputer board for time-course recording through the small diameter coaxial cable 22.

The microcomputer board for time-course recording is provided with a 2.8-inch TFT liquid crystal display and an SD card slot. Values of the fluid pressure sensor are displayed as a time-course graph, and an SD card records the values together with elapsed times. These parts and modules, as well as software for time-course recording of blood pressure values mounted on the microcomputer, were made by using publicly known members. The electronic circuit for transmitting a value of the blood pressure sensor to the microcomputer was also designed in this manner. Hereinbelow, measurement of the maximal tolerant pressure of the deployed embolic composition is described, using the apparatus shown in the lower part of FIG. 1.

Example 6

A microcatheter was inserted from silicone tube piping 17 through a guide, and the tip of the catheter was accessed (placed) inside the blood vessel model 5 (gel tube 5). The components of the blood vessel model and their blending amounts were described in Table 3. At this time, the small valve 16 was kept open, and the simulated serum was delivered from the pump at a rate ranging from 2 to 30 mL per minute. The liquid embolic agent compositions according to the present invention were injected from the microcatheter tip that accessed the inside of the gel tube 5 to block the flow of simulated serum. When the flow toward the outlet piping 7 from the gel tube 5 was sealed, the flow direction of the simulated serum was switched toward the silicon tube piping 17 that serves as the microcatheter insertion port. In this state, the microcatheter was removed from the apparatus. Next, when the small valve 16 is closed, a pressure applied to the simulated serum is transmitted to the fluid pressure sensor input 10, and a value thereof is sent to the microcomputer and recorded. An operator can freely configure the elapsed time from the removal of the catheter to the closing of the small valve 16, with consideration of the type of liquid embolic agent composition subjected to evaluation or the time taken in completing coagulation or adhesion.

TABLE 3

| Gel solution component | Blending amount (per 25 mL) |
| --- | --- |
| Acrylamide | 6.5 g |
| N,N'-dimethylacrylamide | 0.775 mL |
| N,N-methylenebisacrylamide | 0.25 g |
| Sodium chondroitin sulfate | 0.1 g |
| Egg white-derived albumin | 0.1 g |
| Polyvinyl alcohol | 0.1 g |

In the state described above, a fluid pressure of the simulated serum delivered from the pump is applied to the liquid embolic agent composition, which has been coagulated in the blood vessel model. As the fluid pressure value continues to rise, at a certain pressure value, the liquid embolic agent composition deployed in the blood vessel model is finally pushed and migrated toward the drain direction piping 7. At this time, the fluid pressure value is decreasing, and, therefore, the peak value recorded in the microcomputer is defined as the maximal tolerant pressure of the deployed embolic composition. When a pressure equal to or higher than the mechanical durability of the gel tube itself is applied, a breakage of the connecting portions at both ends of the gel tube 5 in FIG. 1, or a rupture of the gel tube 5 itself, is observed. At this time point, the pressure of the simulated serum drops to zero. Generally, a blood pressure applied to a brain blood vessel in a range of 250 to 300 mmHg corresponds to a rupture risk region. Therefore, a detected maximum value of the fluid pressure sensor was set to 400 to 420 mmHg.

Liquid embolic agent compositions of Test Nos. 1 to 10 shown in Table 4 below were prepared, and the tests were carried out.

TABLE 4

| Test No. | Component of embolic agent composition | Blending amount (wt %) | Maximal tolerant pressure of deployment (mmHg) | Post-test state |
| --- | --- | --- | --- | --- |
| 0 | Sodium alginate | 2.0 | 0 ± 1 | Detached and migration |
| 1 | Sodium alginate<br>Carrageenan<br>Methylcellulose | 1.0<br>0.5<br>0.2 | 38 ± 10 | Detached and migration |
| 2 | Sodium alginate<br>Gellan gum | 1.0<br>0.25 | 52 ± 24 | Detached and migration |
| 3 | Sodium alginate<br>Gellan gum<br>Hydroxypropyl cellulose | 1.0<br>0.25<br>0.25 | 112 ± 14 | Detached and migration |
| 4 | Sodium alginate<br>Gellan gum<br>Hydroxypropyl cellulose<br>Polyacrylic acid | 1.0<br>0.25<br>0.25<br>2.5 | 22 ± 19 | Detached and migration |
| 5 | Sodium alginate<br>Gellan gum<br>Hydroxypropyl cellulose<br>Sodium caseinate | 1.0<br>0.25<br>0.25<br>2.0 | 31 ± 11 | Detached and migration |
| 6 | Sodium alginate<br>Gellan gum<br>Hydroxypropyl cellulose<br>Enzyme preparation for food processing | 1.0<br>0.25<br>0.25<br>5.0 | 194 ± 45 | Pressure leak |
| 7 | Sodium alginate<br>Gellan gum<br>Hydroxypropyl cellulose<br>Enzyme preparation for food processing | 1.0<br>0.25<br>0.25<br>8.0 | 278 ± 85 | Rupture of blood vessel model |
| 8 | Sodium alginate<br>Gellan gum<br>Hydroxypropyl cellulose<br>Gelatin | 1.0<br>0.25<br>0.25<br>2.5 | 152 ± 31 | Detached and migration |
| 9 | Sodium alginate<br>Gellan gum<br>Hydroxypropyl cellulose<br>Colloidal silica particles | 1.0<br>0.25<br>0.25<br>2.0 | 41 ± 26 | Pressure leak |
| 10 | Sodium alginate<br>Gellan gum<br>Hydroxypropyl cellulose<br>Poly(N,N-dimethyl) acrylamide | 1.0<br>0.25<br>0.25<br>1.0 | 84 ± 17 | Pressure leak |

Figure 2:
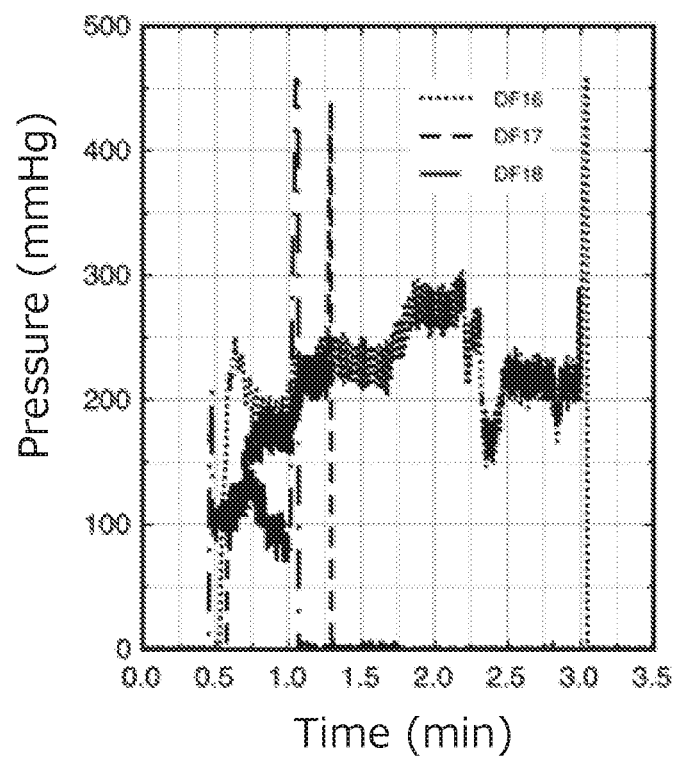
FIG. 2 is a graph showing a test result of pressure leakage of the deployed embolization compositions in the maximal tolerable fluid pressure test.

Table 4 represents the potential combinations of the 10 different types of liquid embolic agents, but it does not means that only the combinations of 1 to 10 were tested. When the value exceeded the maximal tolerant pressure of deployment, the liquid embolic agent composition coagulated in the blood vessel model 5 exhibited two kinds of behaviors. One of behaviors is described as "detached and migration", where the composition was pushed by the pumping pressure, detached, and migrated toward the piping 7. In another kind of behavior, after exceeding the fluid pressure peak, the pressure value fluctuated around a certain value other than zero. This occurred via internal pressure conduction across the pump and the drain side boundaries of the coagulated liquid embolic agent composition, through putative pores or the like produced in the embolic agent composition matrices. Since the conduction occurred through the pores, the fluid pressure value did not drop to zero, and the embolic agent composition was retained inside the blood vessel model 5, neither being pushed nor migrated. This state was described as "pressure leak". FIG. 2 shows test results of typical pressure leak states. In the three test results, all of the recorded states involved the fluid pressure value, where it reached a peak and then descent once before oscillating around a converged value.

As the pressure applied from the pump to the embolic agent composition was increased, at certain value, the rupture of the blood vessel model was also observed without occurrence of pressure leaks. This is the most ideal performance exhibited by an embolic agent because this indicates that the embolic agent composition is firmly adhered to the inner wall of the blood vessel model and that the coagulated embolic agent composition itself is not destroyed by the applied hydraulic pressure. In the results shown in Table 4, the highest value of the maximal tolerant pressure of deployment, i.e., the most superior embolic performance, exhibited a peak value at 278 mmHg (Test No. 7), and the blood vessel model was ruptured at this peak fluid pressure. The pressure transition was recorded in a chart shown in FIG. 3, in which the fluid pressure increased within a few seconds after closing the valve, and the fluid pressure value dropped to zero immediately after the blood vessel model ruptured.

(Test Number 0)

Patent Literature 1 (JP H5-103802 A) describes a use of a high polymer gel as an embolizing material for vascular lesions, such as cerebral aneurysm, in which the high polymer gel is obtained via precipitation of water-soluble polymers with monovalent, anionic functional groups into a polyvalent cation solution. The literature further discloses a method of producing an embolizing material in a solid state, in which an aqueous solution of sodium alginate is extruded into an aqueous solution of calcium chloride to form a high polymer gel. The high polymer gel is immersed in an aqueous solution of sodium chloride and then dried, i.e., water is removed therefrom.

On the other hand, the liquid embolic agent compositions according to the present invention are characterized by being in a liquid state and by exhibiting an embolizing function in vivo through reaction with calcium ions in the blood. Here, in order to compare the liquid embolic agent composition according to the present invention with the vascular lesion embolizing material described in Patent Literature 1, a test was conducted using the liquid embolic agent composition of Test No. 0 in Table 4. In all of the test numbers in Table 4, an isotonic aqueous buffer solution was used to reproduce the osmotic pressure of human plasma, i.e., an aqueous solution containing 0.15 mol/L sodium chloride, 20 mmol/L tris (hydroxymethyl) aminomethane hydrochloride (pH 8.0), and 5.0 mmol/L calcium chloride. The liquid embolic agent composition of Test No. 0 contained only sodium alginate as the component to react with calcium ions. The concentration of sodium alginate was 2.0 wt %, selected to be approximately equal to the concentration of 2.0 w/v % described in Example of Patent Literature 1.

While the above isotonic aqueous buffer solution was perfused, the liquid embolic agent composition of Test No. 0 was injected through a microcatheter into the blood vessel model shown in FIG. 1. As a result, gelation occurred instantaneously due to contact with calcium ions contained in the isotonic aqueous buffer solution. However, the gelated liquid embolic agent composition, i.e., the coagulated embolic composition, did not adhere to the inner wall of the blood vessel model and was pushed and migrated outside of the blood vessel model, along with the perfusion of the isotonic aqueous buffer solution. This result indicates that the function provided by the present invention cannot be obtained by alginates alone. The present inventors repeated trials to solve this problem and identified a set of acidic polysaccharides that can react with calcium ions to gelate. The acidic polysaccharides were combined with an active ingredient of the liquid embolic agent composition that improves the adhesion force to the inner wall of a blood vessel model. Several examples are described with Test Nos. 1 to 10, as marked in Table 4, to demonstrate the performance of the liquid embolic agent compositions.

(Test Nos. 1 and 2)

Hereinbelow, the maximal tolerant pressure of deployment and the state of each liquid embolic agent composition after the test will be described individually according to the test number. The maximal tolerant pressure of deployment of the liquid embolic agent compositions of Test Nos. 1 and 2 were 38±10 mmHg and 52±24 mmHg, respectively. These values are lower than 80 mmHg, the optimum blood pressure value of diastolic blood pressure. Furthermore, after showing these peak values, the coagulated liquid embolic agent compositions detached from the inner wall of the blood vessel model and were pushed and migrated in the pumping direction. From these results, coagulation and adhesive force to an actual blood vessel inner wall surface will be relatively weak, and, thus, an ideal function of the present invention is not provided when the liquid embolic agent compositions of Test No. 1 or 2 are used.

(Test No. 3)

Even in cases of the liquid embolic agent compositions in Test Nos. 1 and 2 were composed of only a calcium ion-entrapping component and an anti-biodegradation component in Test No. 3, by replacing the anti-biodegradation component methylcellulose by hydroxypropyl cellulose the maximal tolerant pressure was improved to 112±14 mmHg. This value is close to 120-129 mmHg as seen in normal values of systolic blood pressure, and, thus, the liquid embolic agent composition described in Test No. 3 is preferable relative to the compositions of Test Nos. 1 and 2.

(Test Nos. 4 and 5)

The liquid embolic agent compositions of Test Nos. 4 and 5 were prepared by the addition of polyacrylic acid and sodium caseinate, respectively, to the liquid embolic agent composition of Test No. 3. They exhibited maximal tolerant pressures of deployment of 22±19 mmHg and 31±11 mmHg in Test No. 4 and Test No. 5, respectively, and both post-test states were detached and migrated. Polyacrylic acid has a carboxyl group capable of entrapping calcium ions. Sodium caseinate is a derivative of the acidic protein casein, where the acidic amino side chain in the intact casein is neutralized to elevate solubility in water. Thus, sodium caseinate can also entrap calcium ions. These properties were expected to modify the performance of the liquid embolic agent composition; however, as indicated by the results, the performances in Test Nos. 4 and 5 were not improved, likely because the acidic polysaccharides from Test No. 3, which provide calcium-entrapping and hydrogel-forming functions, are competitive against polyacrylic acid and sodium caseinate.

(Test Nos. 6 and 7)

The liquid embolic agent compositions of Test Nos. 6 and 7 were prepared by adding the different concentrations of enzyme preparation used for food processing to the liquid embolic agent composition of Test No. 3. The commercially available enzyme preparations for food processing contain an active ingredient enzyme that is capable of crosslinking between protein molecules, and therefore, the enzyme preparations are utilized for various kinds of processing in the food industry. For example, the enzyme preparations are used in a process of binding meat pieces together. These enzyme preparations for food processing also form gels upon dispersion in water, depending on their concentrations. These preparations, however, are not used in such a way during the usual procedures for food processing.

Liquid embolic agent compositions of Test Nos. 6 and 7 exhibited maximal tolerant pressures of deployment as high as 194±45 mmHg and 278±85 mmHg, respectively. These values are greater than the normal systolic and diastolic blood pressures and are in a range defined as high blood pressure. The liquid embolic agent composition of Test No. 6 exhibited a post-test state of pressure leak, while for the liquid embolic agent composition of Test No. 7, the vessel model could not tolerate the increased backpressure of the fluid, which was induced with the blockage by the embolic agent, resulting in rupture. These satisfactory embolization performances were presumably provided by increased mechanical strength via coincident hydrogelation of the enzyme preparation itself and the calcium ion-entrapping components in the liquid embolic agent composition, in parallel with the enhanced adhesive strength of the coagulated composition on the inner wall of the vessel model containing a protein component albumin.

(Test No. 8)

With respect to the liquid embolic agent composition of Test No. 8, the composition of which contained gelatin that has self-gelling properties, like those of the enzyme preparation for food processing, also showed a relatively high value of 152±31 mmHg in the maximal tolerant pressure. This fact indicates that, in the presence of calcium ion-entrapping components, an application of coexistent components capable of hydrogelation by certain chemical stimuli is a factor for providing more preferable embolization performances.

(Test Nos. 9 and 10)

For preparation of the liquid embolic agent composition of Test Nos. 9 and 10, colloidal silica particles and a poly(N,N-dimethyl) acrylamide were added to the liquid embolic agent composition of Test No. 3 (Se'verine Rose, Alexandre Prevoteau, Paul Elzie'rel, Dominique Hourdetl, Alba Marcellan, and Ludwik Leibler, Nanoparticle solutions as adhesives for gels and biological tissues, Nature 505, 382-385, 2014). In the report disclosed by Se'verine Rose et al., colloidal silica particles are capable of adhering hydrogels containing (N, N-dimethyl) acrylamide. These tests were conducted to demonstrate that, just based on the publicly known information, these of known materials cannot provide sufficient performances as described in the present invention.

As a result, the liquid embolic agent composition of Test Nos. 9 and 10 exhibited values of maximal tolerant pressure of deployment of 41±26 mmHg and 84±17 mmHg, respectively. These results are unfavorable as compared with the maximal tolerant pressure achieved by the liquid embolic agent composition of Test No. 3. This result indicates that the performance provided by the present invention is not simply achieved by a combination of publicly known information. A more preferable embolizing performance is exerted only through the functions and mechanisms provided by Patent Literature 2 of the present inventors; that is, the calcium ion-entrapping and the hydrogel gel forming abilities of the active ingredients, as well as coagulation-promoting and anti-biodegradation properties are combined therewith.

The present inventors have discovered a complementary fact that the post-test state "pressure leak" in Test No. 6 can be eliminated by a subsequent injection of the liquid embolic agent composition in Test No. 3 through a microcatheter, a procedure that plugs the small pores causing the leaks. As a result, a high mechanical performance, comparable to the maximal tolerant pressure of deployment of Test No. 7, can be achieved. Thus, the components that comprise the present invention can be combined to enhance the performances of the liquid embolic agent compositions.

CONCLUSION

Figure 3:
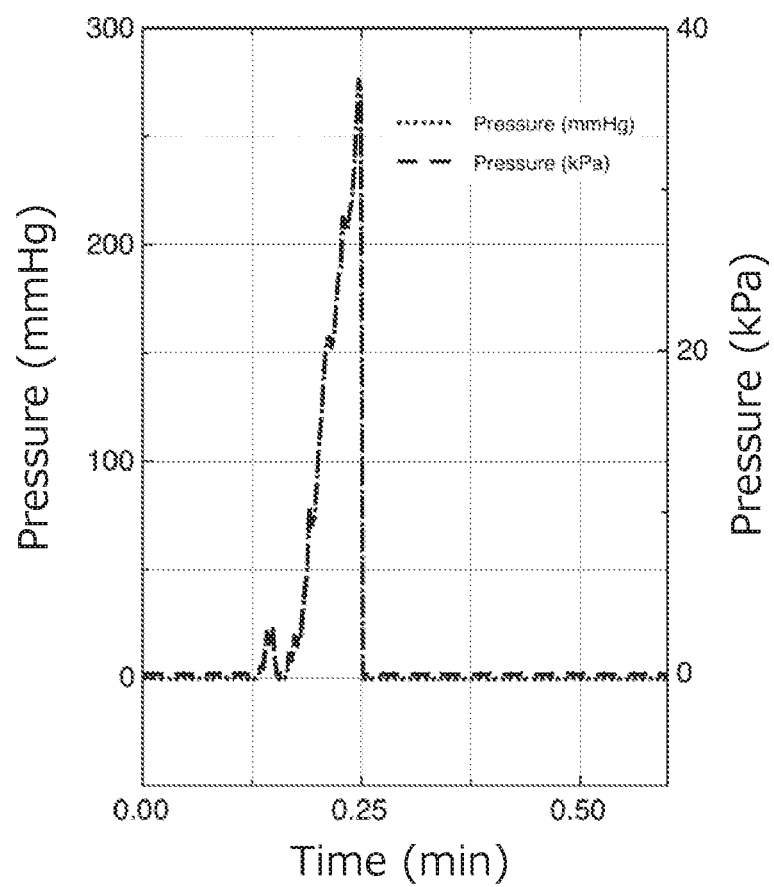
FIG. 3 is a graph that represents pressure change when ruptures of the blood vessel model have occurred during evaluation of maximal tolerant pressure.

According to the present invention, as described above, a liquid embolic agent composition can be produced by combining the active ingredients shown in Table 1. Without using laboratory animals, a blood vessel model can be produced having stable chemical properties as shown in Table 2 and, as shown in Table 4 the performance of liquid embolic agent can be evaluated to provide the compositions that have strong adhesive forces to the inner wall of blood vessels by measuring the maximal tolerant pressure of deployment with the apparatus illustrated in FIG. 1. The performances of the liquid embolic agent compositions are recorded as seen in FIG. 2 and FIG. 3, from which the maximal tolerant pressure deployment can be estimated. Thus, the subjective problems (1) to (5) have been solved by the present invention, and more practical liquid embolic agent compositions have been provided.

REFERENCE SIGNS LIST

1 Silicone rubber stopper
2 Silicone rubber stopper
3 Acrylic rod
4 Glass tube
5 Blood vessel model
6 Connector
7 Silicone tube piping
8 Silicone tube piping
9 T-type stay
10 Fluid pressure sensor input
11 Sensor circuit case
12 Silicone tube piping
13 Connector
14 Silicone tube piping
16 Small valve
17 Silicone tube piping
18 Silicone tube piping
19 Gel tube holder
20 Side unit
21 Sensor stage
22 Small diameter coaxial cable

The invention claimed is:

1. A liquid embolic agent composition which comprises:
a hydrogel forming component having a calcium ion entrapping ability; and
an anti-biodegradable component,
wherein the hydrogel forming component having a calcium ion entrapping ability consists of sodium alginate and gellan gum,
wherein the anti-biodegradable component is hydroxypropyl cellulose,
wherein the liquid embolic agent composition is in a liquid state in vitro,
wherein upon in vivo administration to a living human body, the composition gelates by reacting with calcium ions in blood of said living human body to exhibit a bioadhesiveness in vivo,
wherein the liquid embolic agent composition remains in a liquid state in vitro even when exposed to a temperature the same as that of said living human body, and
wherein in said composition, sodium alginate is present in an amount of 0.5-2.0 wt %, gellan gum is present in an amount of 0.1-0.5 wt %, and hydroxypropyl cellulose is present in an amount of 0.1-5.0 wt %.

2. The liquid embolic agent composition according to claim 1, further comprising a coagulation promoting component, wherein the coagulation promoting component is at least one selected from the group consisting of colloidal silica, poly(N,N-dimethyl) acrylamide, an enzyme preparation for food processing, poly-L-lysine hydrobromide, poly-L-glutamic acid sodium salt, chitosan, and silk fibroin.

3. The liquid embolic agent composition according to claim 1, which is used for treating cerebral aneurysm.

4. The liquid embolic agent composition according to claim 1, which further comprises an iodine type angiographic contrast agent.

5. The liquid embolic agent composition according to claim 1, wherein the gelation occurs at a calcium ion concentration in blood of between 2.5 to 4.0 mM.

6. The liquid embolic agent composition according to claim 2, wherein in said composition, colloidal silica is present in an amount of 0.5-2.0 wt %.

7. The liquid embolic agent composition according to claim 2, wherein in said composition, poly(N,N-dimethyl) acrylamide is present in an amount of 0.1-5.0 wt %.

8. The liquid embolic agent composition according to claim 2, wherein in said composition, an enzyme preparation for food processing is present in an amount of 1.0-10.0 wt %.

9. The liquid embolic agent composition according to claim 2, wherein in said composition, poly-L-lysine hydrobromide is present in an amount of 1.0-5.0 wt %.

10. The liquid embolic agent composition according to claim 2, wherein in said composition, poly-L-glutamic acid sodium salt is present in an amount of 1.0-5.0 wt %.

11. The liquid embolic agent composition according to claim 2, wherein in said composition, chitosan is present in an amount of 0.5-5.0 wt %.

12. The liquid embolic agent composition according to claim 2, wherein in said composition, silk fibroin is present in an amount of 1.0-4.0 wt %.

* * * * *